United States Patent
Lawton et al.

(10) Patent No.: US 9,457,014 B2
(45) Date of Patent: Oct. 4, 2016

(54) CYSTEINE PRODRUGS

(75) Inventors: Daniel Lawton, Bayside, WI (US); Michael Neary, West Allis, WI (US); James A. Nieman, Sherwood Park (CA)

(73) Assignee: Promentis Pharmaceuticals, Inc., Milwaukee, WI (US)

( * ) Notice: Subject to any disclaimer, the term of this patent is extended or adjusted under 35 U.S.C. 154(b) by 204 days.

(21) Appl. No.: 14/391,785

(22) PCT Filed: Jul. 30, 2012

(86) PCT No.: PCT/US2012/048820
§ 371 (c)(1),
(2), (4) Date: Jan. 13, 2015

(87) PCT Pub. No.: WO2013/016727
PCT Pub. Date: Jan. 31, 2013

(65) Prior Publication Data
US 2016/0081987 A1 Mar. 24, 2016

Related U.S. Application Data

(60) Provisional application No. 61/512,751, filed on Jul. 28, 2011.

(51) Int. Cl.
*A61K 38/12* (2006.01)
*A61K 31/426* (2006.01)
*C07D 277/14* (2006.01)
*A61K 31/198* (2006.01)
*A61K 45/06* (2006.01)
*C07D 241/08* (2006.01)
*C07D 267/10* (2006.01)
*C07K 5/062* (2006.01)

(52) U.S. Cl.
CPC ........... *A61K 31/426* (2013.01); *A61K 31/198* (2013.01); *A61K 45/06* (2013.01); *C07D 241/08* (2013.01); *C07D 267/10* (2013.01); *C07D 277/14* (2013.01); *C07K 5/0606* (2013.01)

(58) Field of Classification Search
USPC .......................... 514/1.3, 21.1, 158
See application file for complete search history.

(56) References Cited

U.S. PATENT DOCUMENTS 5,756,481 A 5/1998 Arnal et al.

FOREIGN PATENT DOCUMENTS

GB 2184115 A 6/1987

OTHER PUBLICATIONS

STN database (Apr. 11, 2010, Compound with RN 128586-32-3); supplier Aurora Chemicals.*
RN_1218586-32-3, Chemical Catalog, entered Apr. 11, 2010.
International Preliminary Report on Patentability and Written Opinion, dated Jan. 1, 2014 from corresponding Int'l Application No. PCT/US2012/048820.
International Search Report, dated Nov. 15, 2012 from corresponding Int'l Application No. PCT/US2012/048820.
DB STN on the Web, Nov. 4, 2010, compound with RN 128586-32-3.

* cited by examiner

*Primary Examiner* — Pancham Bakshi
(74) *Attorney, Agent, or Firm* — Wood, Phillips, Katz, Clark & Mortimer

(57) ABSTRACT

Novel cysteine prodrugs and their use in the treatment of diseases and/or conditions, including but not limited to diseases and/or conditions of the Central Nervous System (CNS), including but not limited to schizophrenia, drug craving, drug addiction, bipolar disorder, anxiety, depression, Parkinson's disease, Alzheimer's disease, cognitive dysfunction, multiple sclerosis, Amyotrophic lateral sclerosis (ALS), ischemic stroke, HIV dementia, and Huntington's disease.

2 Claims, No Drawings

CYSTEINE PRODRUGS

FIELD OF THE INVENTION

This invention relates to novel cysteine prodrugs and methods of using these compounds for the treatment of diseases and/or conditions, including but not limited to diseases and/or conditions of the Central Nervous System (CNS), including but not limited to schizophrenia, drug craving, drug addiction, bipolar disorder, anxiety, depression, Parkinson's disease, Alzheimer's disease, cognitive dysfunction, multiple sclerosis, Amyotrophic lateral sclerosis (ALS), ischemic stroke, HIV dementia, and Huntington's disease.

BACKGROUND OF THE INVENTION

Diseases and/or conditions of the Central Nervous System (CNS) affect a large number of people. One of the CNS disorders, schizophrenia, is a debilitating disorder afflicting 1% of the world's population. The development of effective medications to treat schizophrenia relies on advances in characterizing the underlying pathophysiology.

Conventional approaches to treating schizophrenia and other CNS disorders have significant disadvantages, including suboptimal efficacy and/or side effects associated with their use. For example, existing first and second generation antipsychotic agents have a number of shortcomings and significant side effects, such as extrapyramidal side effects, endocrine effects, obesity, elevated triglycerides, blood pressure and glucose levels, type II diabetes, cardiovascular disease, renal toxicity and agranulocytosis. Thus, it is desirable to develop novel agents that can improve treatment outcomes and safety.

Accordingly, there is a significant need for new therapeutical agents to treat disorders of the CNS.

SUMMARY OF THE INVENTION

In one aspect, the present invention is directed to cysteine prodrugs of Formulas I-VII as described below.

In another aspect, the present invention provides methods of treating a disease or condition of the Central Nervous System (CNS), including but not limited to schizophrenia, drug craving, drug addiction, bipolar disorder, anxiety, depression, Parkinson's disease, Alzheimer's disease, cognitive dysfunction, multiple sclerosis, Amyotrophic lateral sclerosis (ALS), ischemic stroke, HIV dementia, and Huntington's disease comprising administering to a subject in need thereof a therapeutically effective amount of any of the inventive compounds.

In some aspects, the methods and compositions of the invention may be used in combination with N-acetyl cysteine (NAC).

Thus, in one embodiment, the invention is directed to a combinational use of: 1) a compound of any of Formulas I-VII and 2) NAC for the treatment of a disease or condition of CNS including but not limited to schizophrenia, drug craving, drug addiction, bipolar disorder, anxiety, depression, Parkinson's disease, Alzheimer's disease, cognitive dysfunction, multiple sclerosis, ALS, ischemic stroke, HIV dementia, and Huntington's disease.

In some aspects, the methods and compositions of the invention may be used in combination with conventional first and second generation anti-psychotic agents.

Thus, in one embodiment, the invention is directed to a combinational use of: 1) a compound of any of Formulas I-VII and/or NAC and 2) pre-existing first generation antipsychotic agents (including but not limited to chlorpromazine, thioridazine, mesoridazine, loxapine, molindone, perphenazine, thiothixene, trifluoperazine, haloperidol, fluphenazine, droperidol, zuclopenthixol and prochlorperazineperphenazine) and/or second generation anti-psychotic agents (including but not limited to amisulpride, aripiprazole, asenapine, blonanserin, clotiapine, clozapine, iloperidone, lurasidone, mosapramine, olanzapine, paliperidone, perospirone, quetiapine, remoxipride, risperidone, sertindole, sulpiride, ziprasidone, zotepine, bifeprunox (DU-127, 090), pimavanserin (ACP-103), and vabicaserin (SCA-136)) for the treatment of a disease or condition of CNS, including but not limited to schizophrenia, drug craving, drug addiction, bipolar disorder, anxiety, depression, Parkinson's disease, Alzheimer's disease, cognitive dysfunction, multiple sclerosis, ALS, ischemic stroke, HIV dementia, and Huntington's disease.

Thus, in one aspect, the present invention is directed to compounds of Formula I:

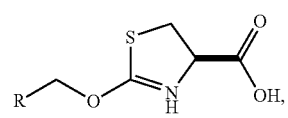

Formula I where
R is selected from the group consisting of alkyl and aryl, preferably from methyl and phenyl.

In another aspect, the present invention is directed to compounds of Formula II:

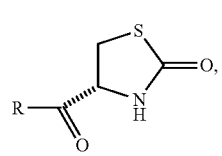

Formula II where R is selected from the group consisting of

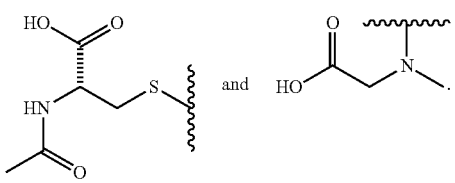

In another aspect, the present invention is directed to compounds of Formula III:

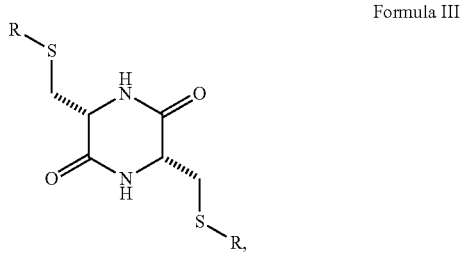

Formula III where R is selected from the group consisting of

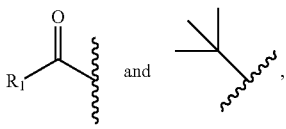

where $R_1$ is alkyl, preferably methyl, or aryl, preferably, phenyl; or $R_1$ comprises an amino acid with the carbonyl.

In another aspect, the present invention is directed to compounds of Formula IV:

Formula IV

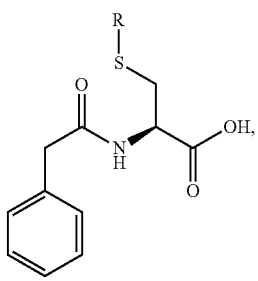

where R is selected from the group consisting of

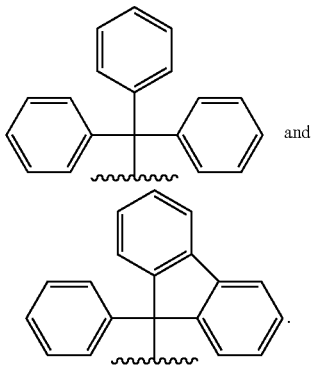

In another aspect, the present invention is directed to the compounds having the following structures:

Formula V

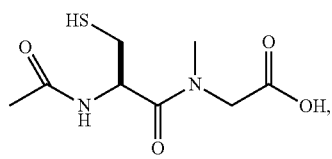

Formula VI

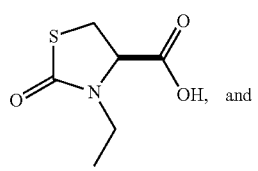

-continued

Formula VII

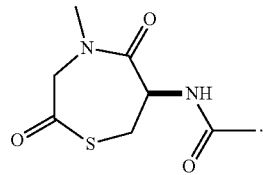

The invention also encompasses pharmaceutically acceptable salts, esters, stereoisomers, enantiomers, and prodrugs of the provided compounds.

A preferred route of administering to the subject is via oral delivery.

In a preferred embodiment, the disease is schizophrenia.

The invention further encompasses pharmaceutical compositions containing a compound of any of Formulas I-VII or a pharmaceutically acceptable salt thereof in combination with a pharmaceutically acceptable carrier.

Methods of formulating/manufacturing such pharmaceutical compositions for the treatment of a disease or condition in a subject are also within the invention's scope.

DETAILED DESCRIPTION OF THE INVENTION

Definitions

The following definitions are used, unless otherwise described.

The term "prodrugs" refers to compounds, including but not limited to monomers and dimers of the compounds of the invention, which become under physiological conditions compounds of the invention or the active moieties of the compounds of the invention.

The term "active moieties" refers to compounds which are pharmaceutically active in vivo, whether or not such compounds are compounds of the invention.

The term "alkyl" refers to a monovalent saturated aliphatic hydrocarbon including straight chain and branched chain groups. Preferably, the alkyl group has 1 to 20 carbon atoms. More preferably, it is a medium alkyl (having 1 to 10 carbon atoms). Most preferably, it is a lower alkyl (having 1 to 4 carbon atoms). The alkyl group may be substituted or unsubstituted.

The term "alkoxy" group refers to both an —O-alkyl and an —O-cycloalkyl group; preferably an alkoxy group refers to a lower alkoxy, and most preferably methoxy or ethoxy.

The term "aryl" refers to a monocyclic or bicyclic aromatic group (e.g., phenyl or naphthyl) that can be unsubstituted or substituted, for example, with one or more, and in particular one to three, substituents, such as halo, alkyl, hydroxy, hydroxyalkyl, alkoxy, alkoxyalkyl, haloalkyl, nitro, amino, alkylamino, acylamino, alkylthio, alkylsulfonyl, and alkylsulfonyl.

The term "heteroaryl" refers to a monocyclic, bicyclic, or tricyclic ring system containing one, two, or three aromatic rings and containing at least one nitrogen, oxygen, or sulfur atom in an aromatic ring, and which can be unsubstituted or substituted, for example, with one or more, and in particular one to three, substituents, such as halo, alkyl, hydroxy, hydroxyalkyl, alkoxy, alkoxyalkyl, haloalkyl, nitro, amino, alkylamino, acylamino, alkylthio, alkylsulfonyl, and alkylsulfonyl. Examples of heteroaryl groups include, but are not limited to, 2H-pyrrolyl, 3H-indolyl, 4H-quinolizinyl, 4H-carbazolyl, acridinyl, benzo[b]thienyl, benzothiazolyl, 13-carbolinyl, carbazolyl, chromenyl, cinnaolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, naptho[2,3-b], oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, and xanthenyl.

The term "phenyl" refers to a cyclic group of atoms with the formula $C_6H_5$ and which can be unsubstituted or substituted, for example, with one or more, and in particular one to three, substituents, such as halo, alkyl, hydroxy, hydroxyalkyl, alkoxy, alkoxyalkyl, haloalkyl, nitro, amino, alkylamino, acylamino, alkylthio, alkylsulfonyl, and alkylsulfonyl.

The term "ester" refers to compounds having a generic structure of $RCO_2R'$, where R and R' are the organic parts of the carboxylic acid and alcohol respectively.

The term "cleavable ester" refers to an ester in which the carboxyl group has been protected by any of the known ester protective groups capable of being removed following the acylation reaction by methods, e.g. chemical or enzymatic hydrolysis, treatment with chemical reducing agents under mild conditions, irradiation with ultraviolet light or catalytic hydrogenation, which do not result in any appreciable destruction of the remaining portion of the molecule. Examples of suitable "cleavable esters" include allyl, trialkylsilyl (e.g. trimethylsilyl) and other esters derived from silyl alcohol or stannyl alcohol which can be removed by solvolysis with a solvent containing hydroxyl groups, t-butoxycarbonyl, benzhydryl, benzyl, p-nitrobenzyl, p-methoxybenzyl, 2,2,2-trichloroethyl, phenacyl, acetonyl, p-bromophenacyl, (lower)alkyl such as methyl, ethyl or t-butyl and the physiologically hydrolyzed esters mentioned above. The general methods for the preparation of these esters and for their removal are described in the literature and are well-known to those skilled in the art.

The term "thioester" refers to a compound with the functional group C—S—CO—C.

The term "dimer" refers to the chemical entity formed by disulfide linkage of two identical prodrugs, or protected cysteine analogs described herein.

The term "composition" is intended to encompass a product comprising the specified ingredients in the specified amounts, as well as any product which results, directly or indirectly, from a combination of the specified ingredients in the specified amounts.

The term "subject" includes mammals, including humans. The terms "patient" and "subject" are used interchangeably.

In general, unless indicated otherwise, a chemical group referred to anywhere in the specification can be optionally substituted.

The term "therapeutically effective amount" means the amount of a compound that, when administered to a subject for treating a disease or disorder, is sufficient to effect such treatment for the disease or disorder. The "therapeutically effective amount" can vary depending on the variety of factors, including the compound, the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

In one embodiment, the terms "treating" or "treatment" refer to ameliorating the disease or disorder (i.e., arresting or reducing the development of the disease or at least one of the clinical symptoms thereof). In another embodiment, "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

The term "combinational use" as used in the present invention encompasses co-formulations of the two active agents as well as co-administration of two active agents as separate formulations.

Description of the Invention

The present invention incorporates and is based on new and emerging scientific understanding of the disorders of the Central Nervous System (CNS). In particular, the present invention is based in part on the understanding of the importance of overcoming metabolic challenges connected with successfully delivering effective moieties of the agents to the CNS. In addition, the present invention is based in part on the recognition that glutamatergic dysfunction plays an important role in the disorders of the CNS. Therefore, it is important that novel agents be able to modulate glutamatergic dysfunction.

In one aspect, the present invention is directed to cysteine prodrugs of Formulas I-VII as described below.

In another aspect, the invention is directed to a method of treating a disease or condition of CNS, including but not limited to schizophrenia, drug craving, drug addiction, bipolar disorder, anxiety, depression, Parkinson's disease, Alzheimer's disease, cognitive dysfunction, multiple sclerosis, ALS, ischemic stroke, HIV dementia, and Huntington's disease in a subject in need thereof comprising administering to the subject a therapeutically effective amount of a compound of any of Formulas I-VII, or a pharmaceutically acceptable salt thereof.

Preferably, diseases or conditions treatable with the compounds of the present invention are related to CNS. In a preferred embodiment, the disease is schizophrenia. In general, the invention is not limited to treatment of any specific disease or condition but encompasses the treatment of any disease or condition whose mechanism may be affected by the compounds of the present invention.

In some aspects, the methods and compositions of the invention may be used in combination with N-acetyl cysteine (NAC).

Thus, in one embodiment, the invention is directed to a combinational use of: 1) a compound of any of Formulas I-VII and 2) NAC for the treatment of a disease or condition of CNS, including but not limited to schizophrenia, drug craving, drug addiction, bipolar disorder, anxiety, depression, Parkinson's disease, Alzheimer's disease, cognitive dysfunction, multiple sclerosis, ALS, ischemic stroke, HIV dementia, and Huntington's disease. In some aspects, the methods and compositions of the invention may be used in combination with conventional first and second generation anti-psychotic agents.

Thus, in one embodiment, the invention is directed to a combinational use of: 1) a compound of any of Formulas I-VII and/or NAC and 2) pre-existing first generation anti-psychotic agents (including but not limited to chlorpromazine, thioridazine, mesoridazine, loxapine, molindone, perphenazine, thiothixene, trifluoperazine, haloperidol, fluphenazine, droperidol, zuclopenthixol and prochlorperazineperphenazine) and/or second generation anti-psychotic agents (including but not limited to amisulpride, aripiprazole, asenapine, blonanserin, clotiapine, clozapine, iloperidone, lurasidone, mosapramine, olanzapine, paliperidone, perospirone, quetiapine, remoxipride, risperidone, sertindole, sulpiride, ziprasidone, zotepine, bifeprunox (DU-127, 090), pimavanserin (ACP-103), and vabicaserin (SCA-136)) for the treatment of a disease or condition of CNS, including but not limited to schizophrenia, drug craving, drug addiction, bipolar disorder, anxiety, depression, Parkinson's disease, Alzheimer's disease, cognitive dysfunction, multiple sclerosis, ALS, ischemic stroke, HIV dementia, and Huntington's disease.

In all described methods, compounds of the present invention, NAC and pre-existing first and second generation anti-psychotic agents are used in therapeutically effective amounts.

In a preferred embodiment, the combinational use of the compounds of the present invention with NAC and/or pre-existing first and/or second generation anti-psychotic agents allows to decrease the therapeutically amount of NAC and/or the pre-existing first and/or second generation anti-psychotic agents that would be necessary to administer without administration of the compounds of the present invention.

The invention also encompasses veterinary use of the provided compounds for CNS disorders in mammals other than humans.

The invention also encompasses the use of the provided compounds as cysteine, cysteine and/or glutathione supplements that can be administered to healthy subjects and/or subjects suffering from a CNS disorder.

Thus, in one aspect, the present invention is directed to compounds of Formula I:

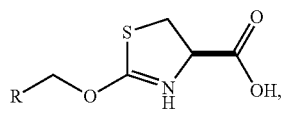

Formula I where
R is selected from the group consisting of alkyl and aryl, preferably from methyl and phenyl.

In another aspect, the present invention is directed to compounds of Formula II:

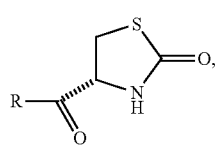

Formula II where
R is selected from the group consisting of

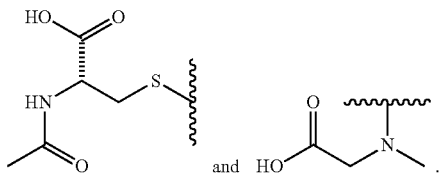

In another aspect, the present invention is directed to compounds of Formula III:

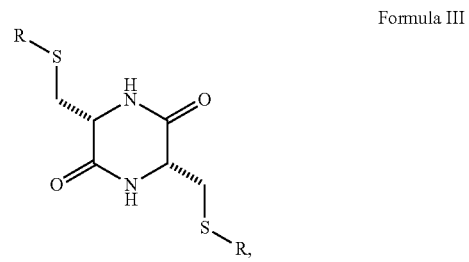

Formula III where R is selected from the group consisting of

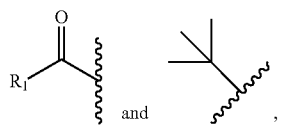

where $R_1$ is alkyl, preferably methyl, or aryl, preferably, phenyl; or $R_1$ comprises an amino acid with the carbonyl.

In another aspect, the present invention is directed to compounds of Formula IV:

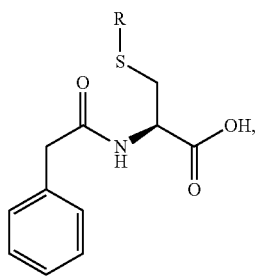

Formula IV where R is selected from the group consisting of

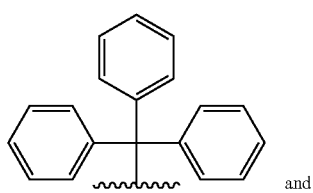

and

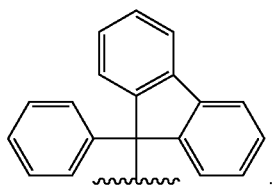

With respect to the compounds of Formula IV, the invention also encompasses compounds where the trityl moiety is replaced with another S-protecting group, for example a thioester, such as acetyl or phenylacetyl.

Also, the invention encompasses mixed dimers of the compounds of Formula IV, including but not limited to, the following compounds:

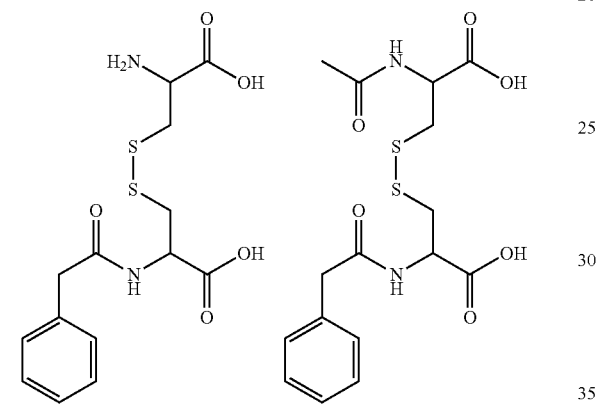

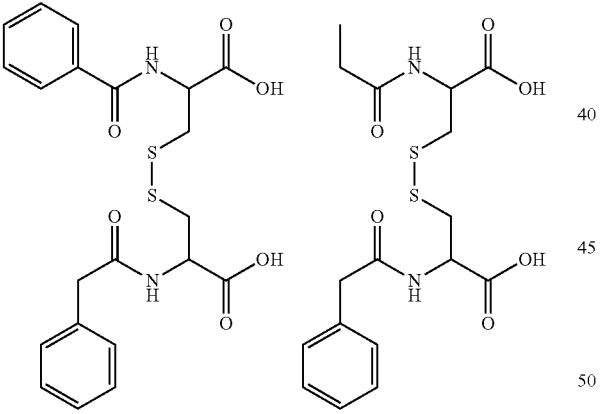

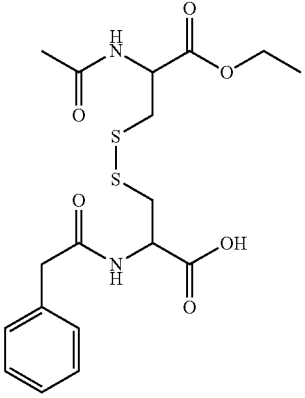

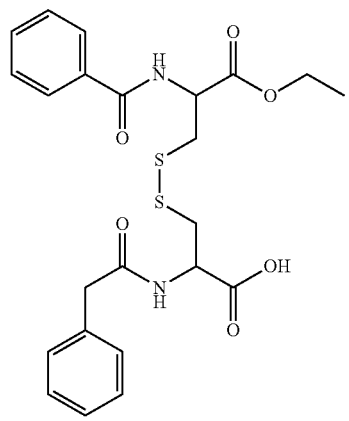

In another aspect, the present invention is directed to the compounds having the following structures:

Formula V

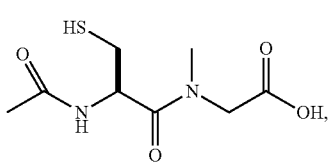

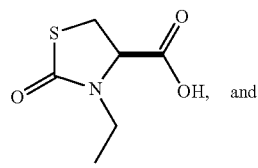

Formula VI

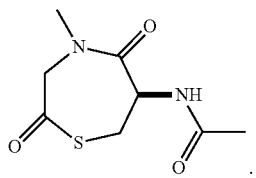

Formula VII

Certain compounds described herein may contain one or more chiral atoms, or may otherwise be capable of existing as two enantiomers, or two or more diastereoisomers.

Accordingly, the compounds of this invention include mixtures of enantiomers/diastereoisomers as well as purified enantiomers/diastereoisomers or enantiomerically/diastereoisomerically enriched mixtures.

Also included within the scope of the invention are the individual isomers of the compounds represented by formulas above as well as any wholly or partially equilibrated mixtures thereof.

The present invention also covers the individual isomers of the compounds represented by the formulas above as mixtures with isomers thereof in which one or more chiral centers are inverted. Also, it is understood that all tautomers and mixtures of tautomers are included within the scope of the compounds of the formulas above.

The compounds of the invention can exist in unsolvated as well as solvated forms, including hydrated forms, e.g., hemi-hydrate. In general, the solvated forms, with pharmaceutically acceptable solvents such as water, ethanol, and the like are equivalent to the unsolvated forms for the purposes of the invention.

Certain compounds of the invention also form pharmaceutically acceptable salts.

The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences*, 1977, 66:1 et seq.

Pharmaceutically acceptable salts include, but are not limited to, acid addition salts. For example, the nitrogen atoms may form salts with acids. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid and citric acid.

Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

The present invention also provides pharmaceutical compositions that comprise compounds of the present invention formulated together with one or more non-toxic pharmaceutically acceptable carriers. The pharmaceutical compositions can be specially formulated for oral administration in solid or liquid form, for parenteral injection or for rectal administration.

The pharmaceutical compositions of this invention can be administered to humans and other mammals orally, rectally, parenterally, intracisternally, intravaginally, transdermally (e.g. using a patch), transmucosally, sublingually, pulmonary, intraperitoneally, topically (as by powders, ointments or drops), bucally or as an oral or nasal spray. The term "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes one or more compounds as described above formulated into compositions together with one or more non-toxic physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

Compositions suitable for parenteral injection may comprise physiologically acceptable, sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Ophthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients.

The total daily dose of the compounds of this invention administered to a human or lower animal may range from about 0.0001 to about 1000 mg/kg/day. If desired, the effective daily dose can be divided into multiple doses for purposes of administration; consequently, single dose compositions may contain such amounts or submultiples thereof to make up the daily dose.

For a clearer understanding of the invention, details are provided below. These are merely illustrations and are not to be understood as limiting the scope of the invention in any way. Indeed, various modifications of the invention in addition to those shown and described herein will become apparent to those skilled in the art from the following examples and foregoing description. Such modifications are also intended to fall within the scope of the appended claims.

EXAMPLES

Example 1

Effect of a Drug on Cystine, Cysteine and Glutathione Levels (Prophetic)

Part 1A

The purpose of this experiment is to provide data to support the conclusion that the compounds of the invention increase the levels of cysteine and cystine in normal systems, and in glutathione-deficient systems also increase the levels of glutathione.

A prodrug (0-90 mg/kg, po) will be administered to rats and tissue levels of cystine, cysteine, and glutathione in multiple regions of the brain (at least the striatum and prefrontal cortex) will be measured using HPLC with electrochemical detection. This experiment will be conducted across time (0.5, 1, 2, 4, & 8 hr) to ensure that changes in cystine and glutathione do not simply vary as a function of time (e.g, the glutathione effects take longer to materialize).

It is believed that the experiment will repeat earlier observations that the compounds increase cysteine and cystine in normal systems, and in glutathione-deficient systems also increase the levels of glutathione relative to rats receiving vehicle without a drug.

Part 1B

The next part of the experiment will be to create a condition whereby tissue levels of glutathione are diminished to demonstrate that the elevated levels of cystine in the cell would be used to restore/maintain glutathione levels.

This can be examined in at least two ways.

First, the experiment described in part 1A is repeated, except the harvested tissue is exposed to agents that induce oxidative stress which would prompt the cells to use/increase the synthesis of glutathione (the details are provided below). Specifically, the inventors have found that iron (0-120 min exposure to 0-100 microM) and ethacrynic acid (0-30 min exposure to 0-10 microM) decrease tissue levels of glutathione in cultured cells.

The expected result from this experiment is that accumulation of cystine inside the cell will be used to maintain glutathione levels. Thus, it is expected that the prodrug treatment conditions (dose, and pretreatment time prior to harvesting the tissue) that produced the peak increase in tissue cystine levels in the first experiment would be the most effective in maintaining normal glutathione levels even in the face of oxidative stress.

Second, the inventors have found that rats in the MAM neurodevelopmental model of schizophrenia (described in detail below) express a modest reduction in tissue levels of glutathione—thus providing a second model of impaired glutathione function that may enable testing the premise that some prodrugs only restore glutathione levels without promoting accumulation of glutathione under normal conditions. This approach would have the added benefit of allowing assessing the impact of the compounds on cognitive changes that are thought to be relevant to schizophrenia. Thus, one would be able to test the hypothesis that the conditions that normalize glutathione are also conditions that are expected to improve cognitive performance. Attentional Set Shifting, which is a cognitive task that reflects a deficit in MAM-treated rats that can be restored using NAC, is described in detail below.

If the expected results are obtained, this would convincingly demonstrate the conditions needed for prodrugs to elevate levels of glutathione. The current thinking is that the rate-limiting step in glutathione synthesis is cystine availability in the cell. The obtained data would advance this understanding by demonstrating the importance of other factors, namely the depletion of glutathione.

Tissue Assay

The tissue punches (1 mm punches will be taken from either the striatum or the medial prefrontal cortex) will be homogenized in a buffer solution used to prevent the degradation of thiols. One fraction will be used to determine protein content and the other fraction will be used to determine thiol content using HPLC with EC detection (eg, Decade II, reactor cell, −1.4V; Flex Cell +0.65V, Antec Leyden, Netherlands).

MAM

Timed pregnant Sprauge-Dawley rats are given an acute injection of methylazoxymethanol (MAM; 22 mg/kg, IP) or vehicle on gestational day 17. Following vaginal birth, all mothers and offspring are left undisturbed until weaning on postnatal day 22.

Attentional Set Shifting

Seven days prior to testing the animals will be food deprived to 85% of their free-feeding weight. Rats will be trained and tested on a four-arm cross maze (60×20×12 inches), constructed from Plexiglas with a removable arm to form a "T" configuration. On the first habituation day, the rat will be allowed to explore and consume up to 20 sugar pellets for 15 minutes. On the second day, the maze will be baited with 12 pellets for 15 minutes. On subsequent days, only one pellet will be placed at the end of each arm. This procedure will be continued daily until the rat consumes 16 sugar pellets in 15 minutes. Once achieved, the turn bias will be determined by forming a "T" configuration with the removable arm. A black-and-white piece of laminated paper for a visual cue will be placed on the floor in one of the arms. One pellet will be placed in each food well of the "T" arms. The rat will then be placed in the stem arm and allowed to choose between the two arms. Cognitive performance will be examined over the following three day period.

Day 1: Visual-cue learning: Rats will be trained to enter the "T" maze arm containing the visual cue. Each trial began with the placement of the rat in one of three arms. The rat will then be permitted to enter one of the two arms and consume the sugar pellet. The visual cue will be placed in each arm 50% of the time. Trials will continue until 10 consecutive correct choices are made. Once achieved, the rat will undergo a probe trial where placement begins in the arm which was not previously used. A correct choice on the probe trial will concluded testing. An incorrect choice will result in continued training as before, however only a criterion of five correct trials will be required before the administration of a subsequent probe trial.

Day 2: Response discrimination: On the second day, animals will be required to choose the arm in the opposite direction of their turn bias regardless of visual cue placement. The visual cue will be placed in each arm for an equal number of trials. All other criterion and aspects of training will be identical to those used on Day 1. On probe trials, the visual cue will be placed in the arm opposite to the direction the rat was required to turn.

Day 3: Reversal learning:

For the response reversal, animals have to turn opposite to the direction that resulted in reinforcement during day 2.

Example 2

Synthesis of the Claimed Compounds (Prophetic)

Exemplary synthetic strategies are outlined in Schemes 1-5 which yield procysteine-like compounds according to the present invention.

No representation has been made that the actual synthesis has been performed. However, it is believed that a person of skill in the art would know how to synthesize the claimed compounds based, in part, on the provided Schemes 1-5.

Scheme 1

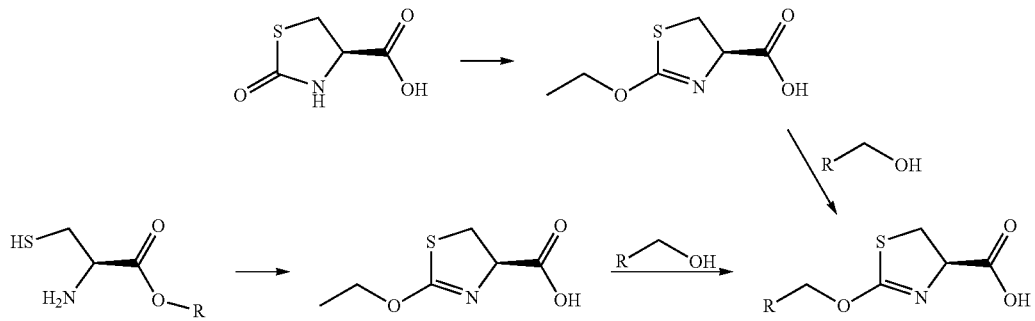

R is selected from the group consisting of alkyl (preferably, methyl) and aryl (preferably, phenyl).

Description of Reactions in Scheme 1

Transformation of L-2-oxo-4-thiazolidinecarboxylic acid to (4R)-2-ethoxy-4,5-dihydro-thiazole-4-carboxylic acid using oxygen alkylating conditions can be achieved by multiple protocols by those skilled in the art. One such example is the application of triethyloxonium tetrafluoroborate in a suitable solvent, such as dichloromethane, potentially in the presence of a base, such as cesium carbonate. Alternatively, protection of the acid with a labile group, such as its allyl or 2-trimethylsilylethyl ester, followed by the application of oxygen alkylating conditions, such as using triethyloxonium tetrafluoroborate, followed by chemoselective cleavage of the ester, such as with palladium or fluoride respectively, will generate (4R)-2-ethoxy-4,5-dihydro-thiazole-4-carboxylic acid. Another approach uses L-cysteine, its salt or its suitably protected ester in contact with tetraethyl orthocarbonate in the presence of a mild base, such as sodium acetate, at elevated temperatures, such as 80 to 100° C., followed by chemoselective removal of the ester or protonation of the carboxylic acid will also generate (4R)-2-ethoxy-4,5-dihydro-thiazole-4-carboxylic acid. Conversion of the (4R)-2-ethoxy-4,5-dihydro-thiazole-4-carboxylic acid into alternate alkyloxy derivatives, for example benzyl, can be accomplished by heating in the presence of excess of the appropriate alcohol, such as benzyl alcohol.

of L-cysteine can be accomplished by self coupling of two molecules of S-tert-butyl-Lcysteine facilitated by a coupling agent, such as 2-(1H-7-azabenzotriazol-1-yl)-1,1,3,3-tetramethyl uronium hexafluorophosphate, in the presence of a base, such as triethylamine, in a suitable solvent, such as DMF. Alternatively, coupling of differentially functionalized S-tert-butyl-L-cysteine, for example with a methyl ester and Fmoc, using a peptide coupling agent, such as 2-(1H-7-

Scheme 2

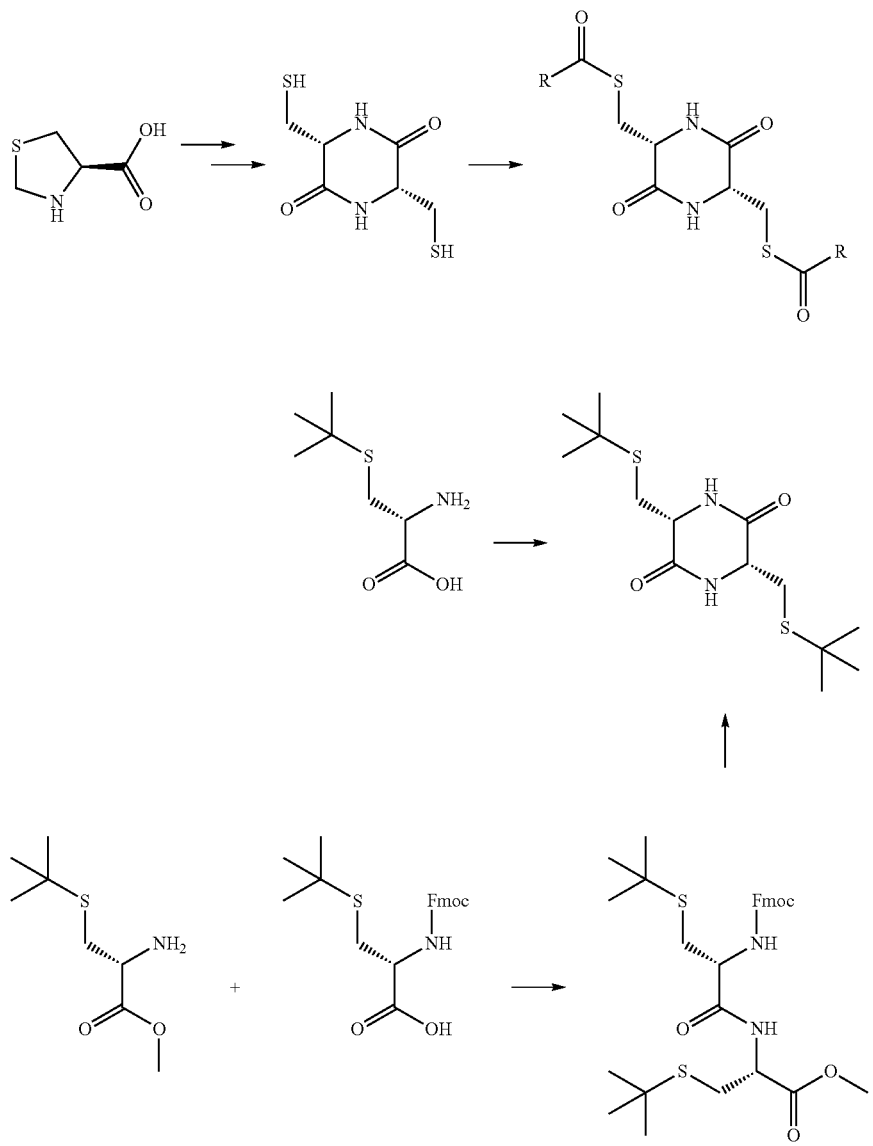

R is chosen from alkyl, aryl, or heteroaryl or together with the carbonyl it can comprise an amino acid.

Description of Reactions in Scheme 2

Using literature protocols, such as Iannotta, Daniela et al, Tetrahedron Letters, 2010, 51 4558-4559, or a related approach, L-thiazolidine-4-carboxylic acid is converted to the symmetrical diketopiperazine of cysteine. Acylation of the free thiols can be accomplished with, for example, acetyl chloride (R=methyl) or benzoyl chloride (R=phenyl), in the presence of a base, such as triethylamine, in a suitable solvent. Formation of the S,S-di-tert-butyldiketopiperazine azabenzotriazol-1-yl)-1,1,3,3-tetramethyl uronium hexafluorophosphate, in the presence of a base, such as triethylamine, in a suitable solvent, such as THF, forms the pre-cyclized di-S,S-di-tert-butyl-L-cysteine dipeptide. Liberation of the N-terminus amine, for example by removal of the Fmoc group with piperidine, followed by subjecting a solution of the resulting primary amine to elevated temperatures will result in diketopiperzine formation generating the symmetrical S,S-di-tert-butyl diketopiperazine of L-cysteine.

Scheme 3A

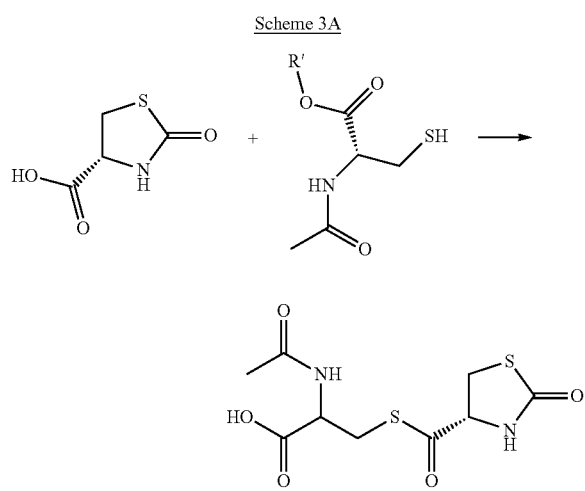

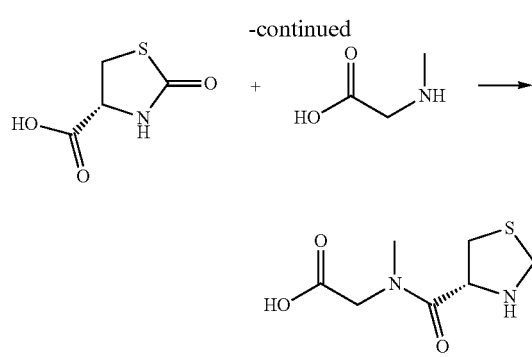

R' is a readily cleavable ester, including but not limited to allyl.

Description of Reactions in Scheme 3A

L-2-Oxo-4-thiazolidinecarboxylic acid can be converted to an activated ester, with for example bis(2-oxo-3-oxazolidinyl)phosphonic chloride in the presence of a base like triethylamine, and contacted with N-acetyl-L-cysteine or its ester, such as the allyl, in the presence of a base, such as triethylamine, generating the thioester. If the N-acetyl-L-cysteine is utilized protonation will generate acid 2-acetylamino-3-(2-oxo-thiazolidine-4-carbonylsulfanyl)-propionic acid, while if an ester of N-acetyl-L-cysteine is employed its cleavage, such as with palladium (0) for the allyl ester, will generate the compound 2-acetylamino-3-(2-oxo-thiazolidine-4-carbonylsulfanyl)-propionic acid. The activate ester generated by contacting L-2-oxo-4-thiazolidinecarboxylic acid with an activating agent, such as bis(2-oxo-3-oxazolidinyl)phosphonic chloride in the presence of a base like triethylamine, can be contacted with sarcosine to generate [methyl-((4R)-2-oxo-thiazolidine-4-carbonyl)-amino]-acetic acid. Numerous alternate methods to activate L-2-oxo-4-thiazolidinecarboxylic acid for coupling to generate its corresponding thioester or amide can be envisioned by those skilled in the art, one such non-exclusive example is by generating its benzotriazole utilizing thionyl chloride in an analogous manner to that detailed by Alan R. Katritzky and coworkers in The Journal of Organic Chemistry (2011), volume 76, page 85-96.

Scheme 3B

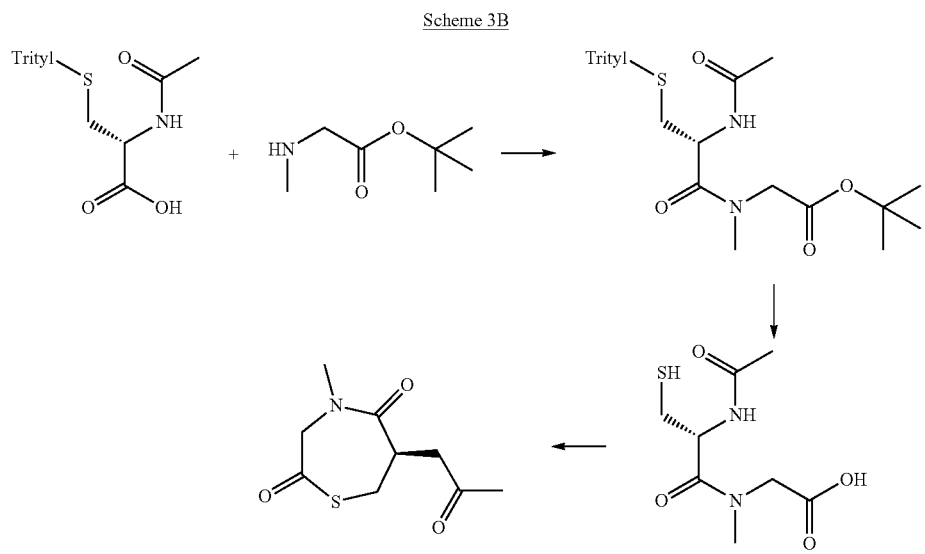

Description of Reactions in Scheme 3B

S-Trityl-N-acetyl-L-cysteine and t-butyl ester of N-methylglycine in the presence of a coupling agent, such as 2-(1H-7-azabenzotriazol-1-yl)-1,1,3,3-tetramethyl uronium hexafluorophosphate, in the presence of a base, such as triethylamine, in a suitable solvent, such as DMF, will generate the corresponding dipeptide. Removal of the tert-butyl ester and trityl group with acidic conditions, such as contact with trifluoroacetic acid in the presence of triethylsilane, generate the penultimate intermediate. Cyclization occurs by activation of the acid, such as by 2,2'-dipyridyldisulfide and triphenylphosphine (see, for example, U.S. Pat. No. 4,287,203) or dicyclohexylcarbodiimide (see, Ura, Yasuyuki et al, Organic and Biomolecular Chemistry; vol. 7; nb. 14; (2009); p. 2878-2884), in an appropriate solvent, such as toluene or dichloromethane, generating N-(4-methyl-2,5-dioxo-[1,4]thiazepan-6-yl)-acetamide.

Scheme 4

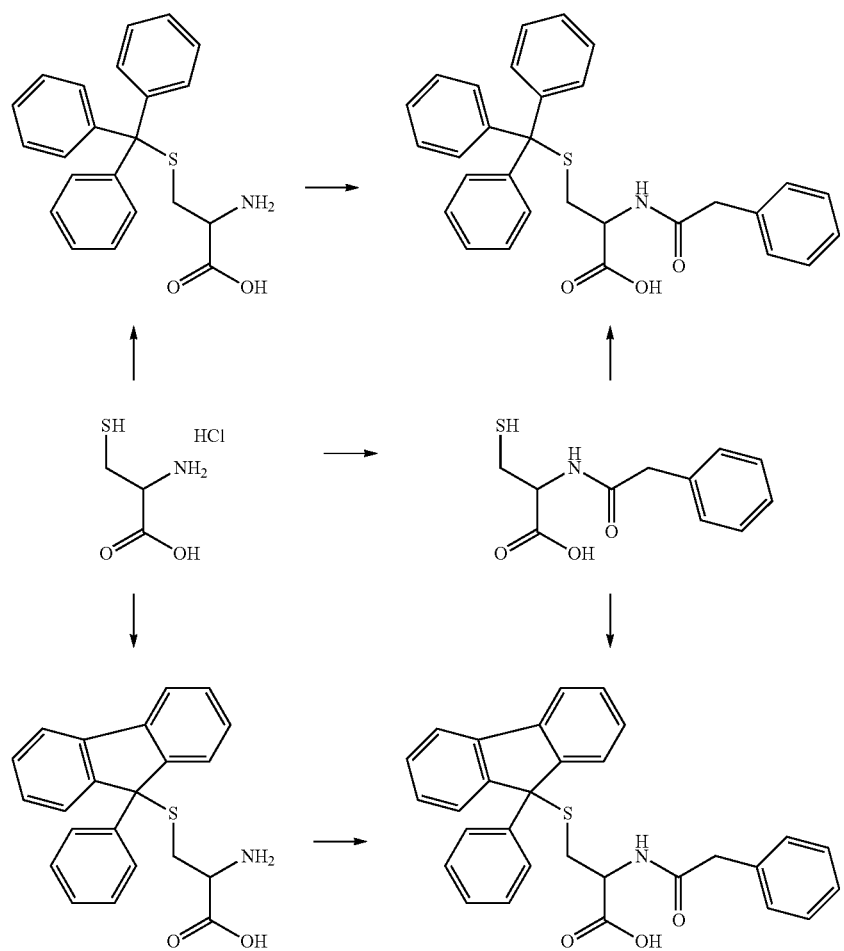

Description of Reactions in Scheme 4

Cysteine, in contact with an acid, such as trifluoroacetic acid or boron trifluoride, and trityl alcohol or 9-phenyl-9-fluorenol, produces the S-trityl or S-(9-phenylfluoren-9-yl) cysteine, respectively (see, Wolfe, Saul et al, Canadian Journal of Chemistry, 1981, 59, 460-421 and Zee-Cheng, K.-Y. et al, Journal of Medicinal Chemistry 1970, 13, 414-418). Contact of the resulting S-trityl or S-(9-phenylfluoren-9-yl) cysteine with phenylacetic acid derivative, such as its anhydride or acid chloride, in the presence of a base, such as triethylamine, produces the corresponding phenylacetamide product. Alternatively, the phenylacetamide of cysteine can be generated by coupling the amine with an activated form of phenylacetic acid, such as it anhydride or acid chloride or acid with peptide coupling agent, in the presence of a base, such as triethylamine. The phenylacetamide of cysteine can be S-functionalized by contact with an acid, such as trifluoroacetic acid or boron trifluoride, and trityl alcohol or 9-phenyl-9-fluorenol producing the S-trityl or S-(9-phenylfluoren-9-yl) version of phenylacetamide of cysteine, respectively.

Scheme 5

Description of Reaction in Scheme 5

Treatment of L-2-oxo-4-thiazolidinecarboxylic acid analogously to the process described in Seki, Masahiko et al, Chemistry—A European Journal, 2004, vol. 10, p. 6102-6110 with a base, such as sodium hydroxide, in a suitable solvent, such as DMSO, in the presence of an ethylating agent, such as ethyl iodide will generate (4R)-3-ethyl-2-oxo-thiazolidine-4-carboxylic acid (N39).

Example 3

Synthesis of Mixed Dimers of Compounds of Formula IV (Prophetic)

Exemplary synthetic strategies are outlined below which yield mixed dimers of compounds of Formula IV according to the present invention.

No representation has been made that the actual synthesis has been performed. However, it is believed that a person of skill in the art would know how to synthesize these compounds based, in part, on the provided synthetic strategies.

Scheme 6

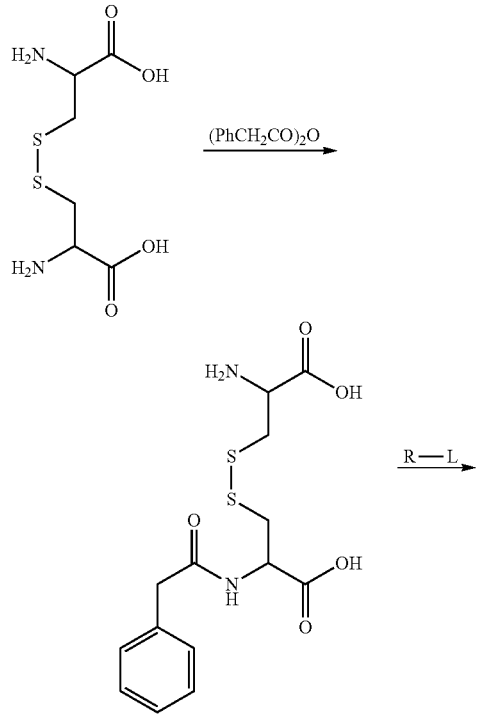

R is preferably H,

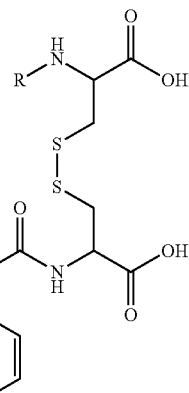

Reaction of cystine with one equivalent of an acylating agent, for example, phenylacetic anhydride, followed by reaction of the primary amine with the appropriate agent containing a leaving group, L, will generate the desired mixed dimer, or the ammonium salt in the case of R=H.

Scheme 7

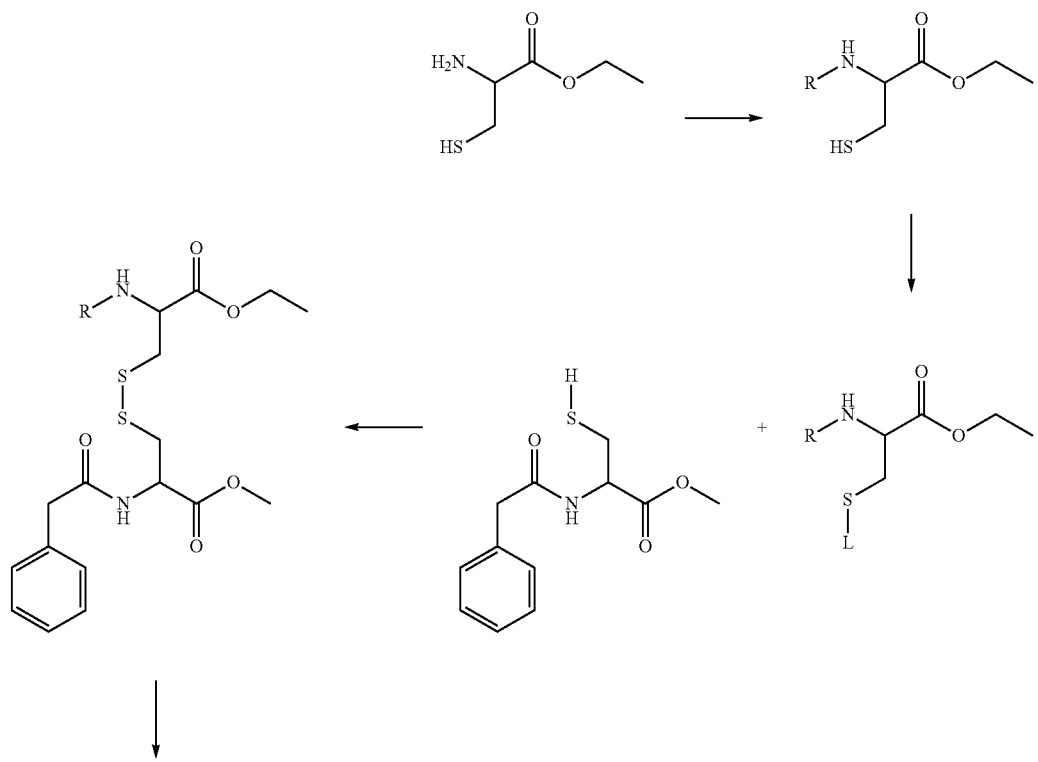

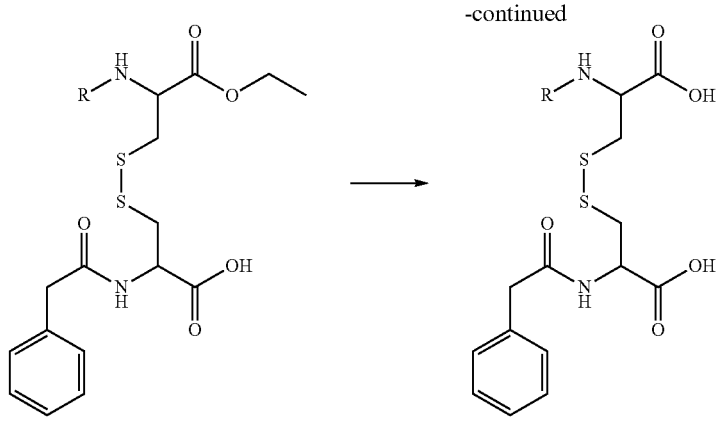

-continued

R is preferably H,

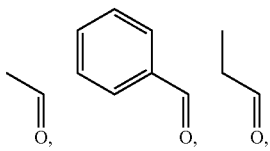

or benzyl-CO.

Incorporation of the appropriate R group onto ethyl cysteine will generate the appropriately functionalized ethyl cysteine. Activation of the sulfur for dimer formation by incorporation of a leaving group is then performed. One method as a non-exclusive example is to apply the protocol by Orrillo, A. Gaston et al, Chemical Communications, 2008, 42, 5298-5300, where L is $S(CH_2)_4CH_3$. Reaction of the activated sulfur with the methyl ester of phenylacetamide or cysteine in the presence of a base, such as triethylamine will generate the mixed dimer as its diester. Selective removal of the methyl ester using saponification protocols known to those skilled in the art, such as lithium hydroxide in a dioxane—water mixture, generates the mono ethyl ester of the dimer. Removal of the ethyl ester by saponification conditions known to those skilled in the art, such as sodium hydroxide in ethanol—water mixture, generates the mixed dimer of cysteine with different N-substitutions.

Scheme 8

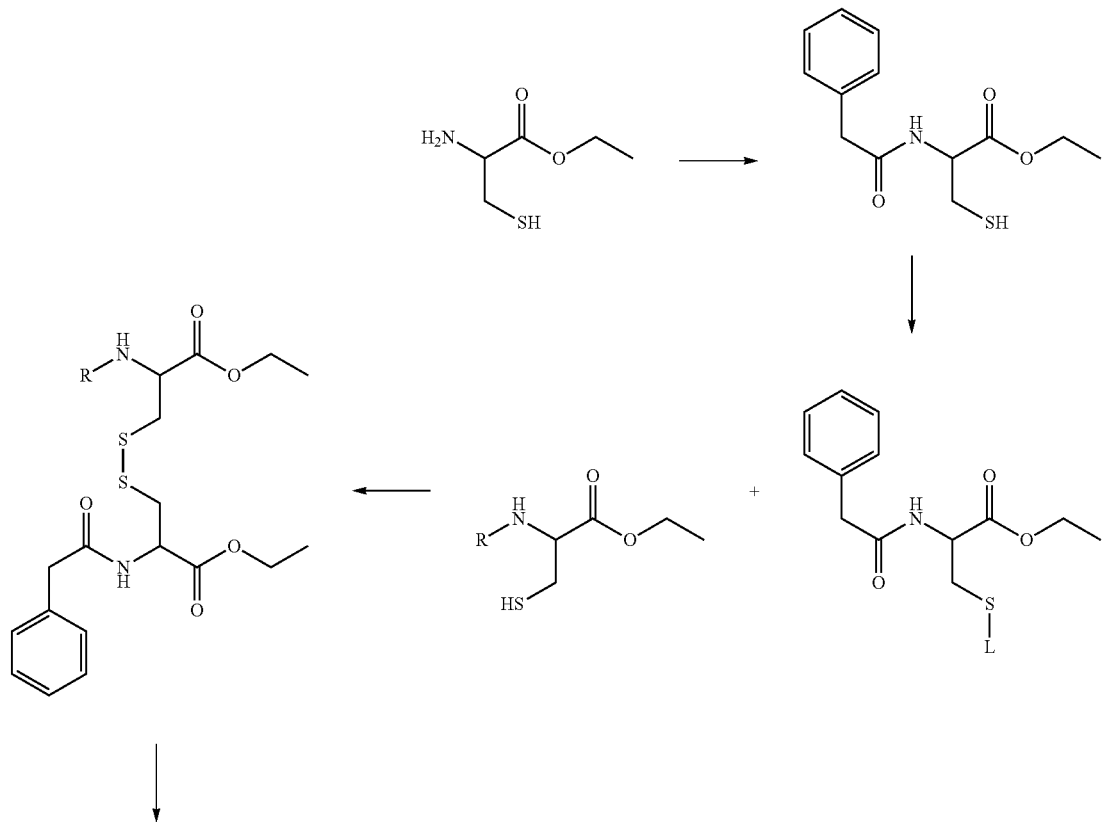

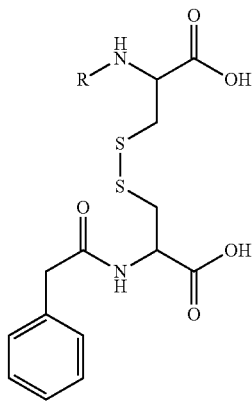

R is preferably H,

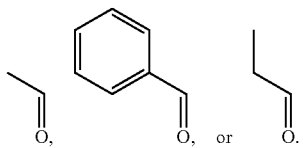

Incorporation of the phenylacetyl group onto the nitrogen of ethyl cysteine, such as by contacting with phenylacetic anhydride, generates the phenylacetamide version of ethyl cysteine. Activation of the sulfur for dimer formation by incorporation of a leaving group is then performed. One method as a non-exclusive example is to apply the protocol by Orrillo, A. Gaston et al, Chemical Communications, 2008, 42, 5298-5300, where L is $S(CH_2)_4CH_3$. Reaction of the actived sulfur with the ethyl ester of the appropriately substituted cysteine in the presence of a base, such as triethylamine, will generate the diethyl ester of the mixed dimer. Removal of the ethyl esters by saponification conditions known to those skilled in the art, such as sodium hydroxide in ethanol-water mixture, generates the mixed dimer of cysteine with different N-substitutions.

The invention claimed is:

1. A compound of formula (VIII),

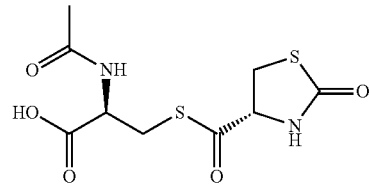 [SMILES: CC(=O)N[C@@H](CSC(=O)[C@@H]1CSC(=O)N1)C(=O)O]

or a pharmaceutically acceptable salt or ester thereof.

2. A pharmaceutical composition comprising a compound of claim 1 and a pharmaceutically acceptable carrier.

* * * * *